(12) United States Patent
Patil

(10) Patent No.: US 9,949,364 B2
(45) Date of Patent: Apr. 17, 2018

(54) ASSEMBLY METHODS AND APPARATUS FOR ELECTRICALLY STABLE CONNECTORS

(71) Applicant: Angiometrix Corporation, Bethesda, MD (US)

(72) Inventor: Nitin Patil, Albany, CA (US)

(73) Assignee: Angiometrix Corporation, Bethesda, MD (US)

( * ) Notice: Subject to any disclaimer, the term of this patent is extended or adjusted under 35 U.S.C. 154(b) by 0 days.

(21) Appl. No.: 15/189,414

(22) Filed: Jun. 22, 2016

(65) Prior Publication Data

US 2016/0309586 A1    Oct. 20, 2016

Related U.S. Application Data

(63) Continuation of application No. PCT/US2015/013077, filed on Jan. 27, 2015.

(60) Provisional application No. 61/931,862, filed on Jan. 27, 2014.

(51) Int. Cl.
| | |
|---|---|
| *H05K 1/02* | (2006.01) |
| *A61B 5/00* | (2006.01) |
| *H05K 1/11* | (2006.01) |
| *H05K 3/10* | (2006.01) |
| *H05K 3/46* | (2006.01) |
| *A61M 25/09* | (2006.01) |

(52) U.S. Cl.
CPC ......... *H05K 1/0268* (2013.01); *A61B 5/6851* (2013.01); *A61M 25/09* (2013.01); *H05K 1/0296* (2013.01); *H05K 1/118* (2013.01); *H05K 3/10* (2013.01); *H05K 3/4644* (2013.01); *A61B 2562/12* (2013.01); *A61M 2025/09108* (2013.01); *H05K 2201/09481* (2013.01); *H05K 2201/09709* (2013.01)

(58) Field of Classification Search
CPC .................................................. H05K 1/0268
See application file for complete search history.

(56) References Cited

U.S. PATENT DOCUMENTS

| | | |
|---|---|---|
| 2005/0061540 A1 | 3/2005 | Parker et al. |
| 2006/0091994 A1 | 5/2006 | Nelson |
| 2006/0097737 A1 | 5/2006 | Parker et al. |
| 2006/0103405 A1* | 5/2006 | Parker ............... G01R 31/2808 324/755.01 |

(Continued)

*Primary Examiner* — Jeremy C Norris
(74) *Attorney, Agent, or Firm* — Levine Bagade Han LLP

(57) ABSTRACT

Assembly methods and apparatus for electrically stable connectors are described herein where a conductive wire assembly generally comprises an insulative substrate having a length, one or more conductive elements formed along a first direction upon the substrate, an insulative coverlay formed upon the one or more conductive elements, and at least one opening or window defined through the insulative coverlay exposing a portion of the one or more conductive elements. A conductive coating is formed upon the insulative coverlay such that the conductive coating is in contact with the portion of the one or more conductive elements through the at least one opening or window and the conductive coating may have at least one region removed along a second direction in proximity to the at least one opening or window such that one or more conductive pads are formed and are electrically isolated from a remainder of the conductive coating.

41 Claims, 15 Drawing Sheets

(56) References Cited

U.S. PATENT DOCUMENTS

2011/0028816 A1 2/2011 Simpson et al.
2011/0230735 A1 9/2011 Wolfe et al.
2011/0306867 A1 12/2011 Gopinathan et al.

* cited by examiner

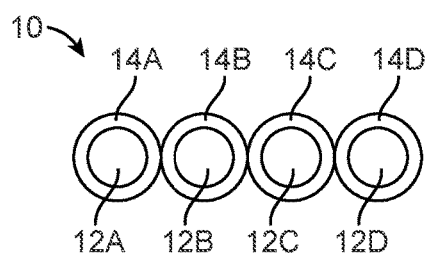
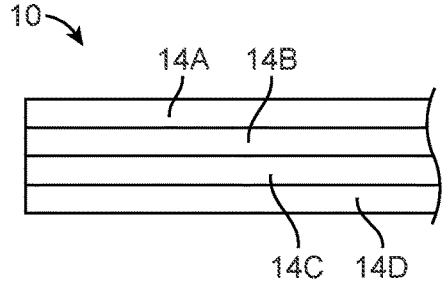
FIG. 1A    FIG. 1B
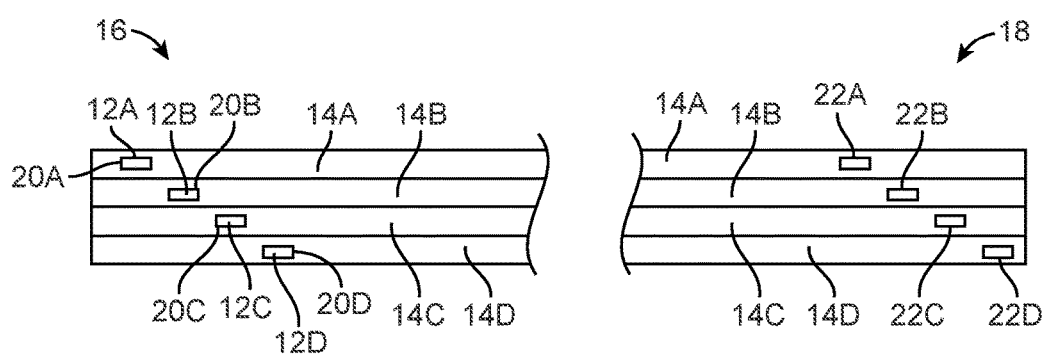
FIG. 2A
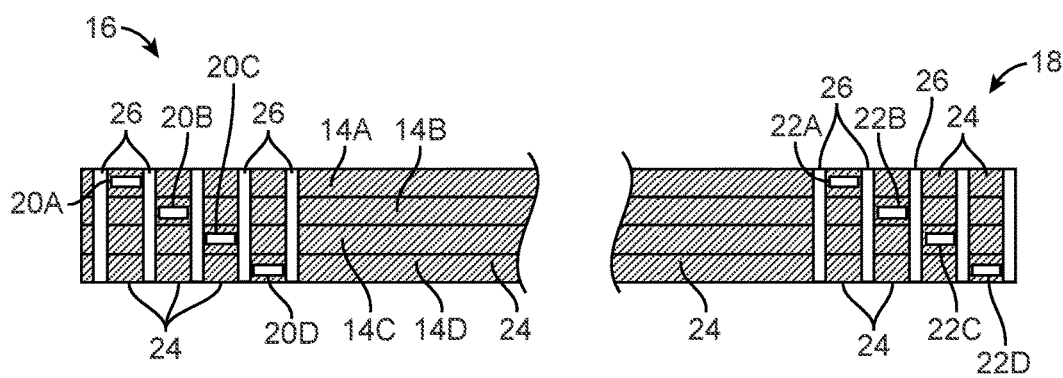
FIG. 2B

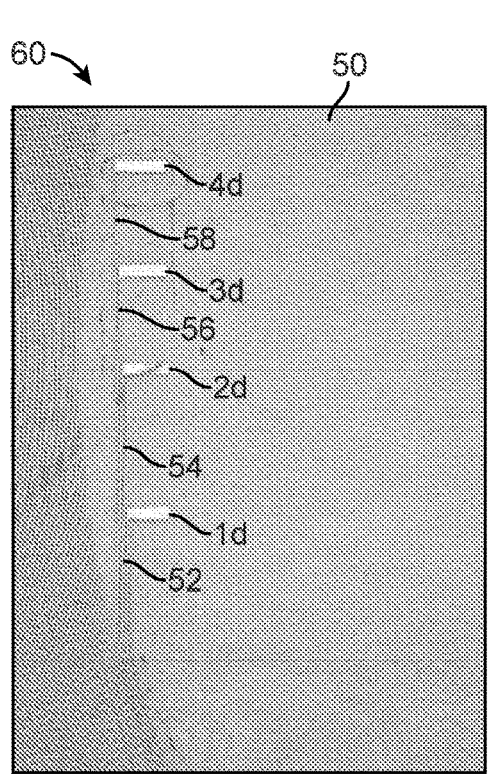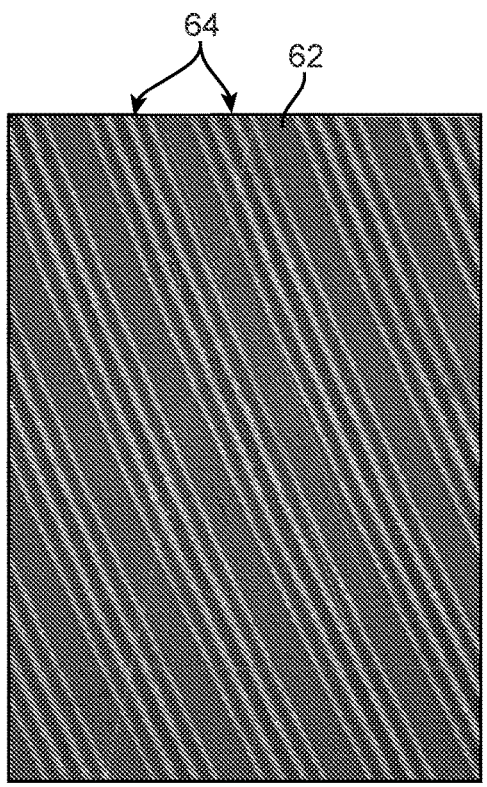
FIG. 7A         FIG. 7B
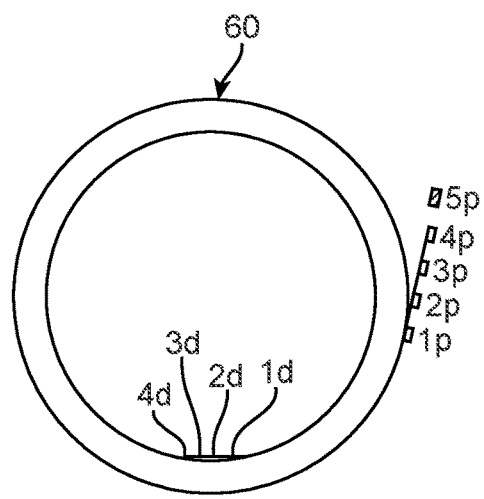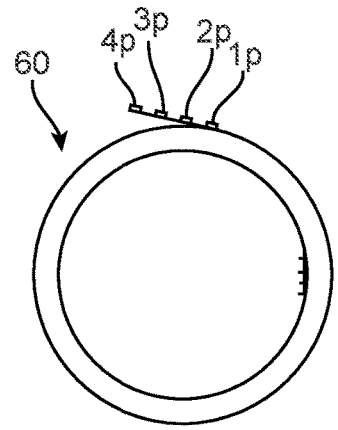
FIG. 8A         FIG. 8B

ASSEMBLY METHODS AND APPARATUS FOR ELECTRICALLY STABLE CONNECTORS

CROSS-REFERENCE TO RELATED APPLICATIONS

This application is a continuation of PCT International Application No. PCT/US2015/013077 filed Jan. 27, 2015, which claims the benefit of priority to U.S. Prov. 61/931,862 filed Jan. 27, 2014, each of which is incorporated herein by reference in its entirety.

FIELD OF THE INVENTION

The present invention relates to methods and apparatus for the assembly and construction of conducting elements in the form of wires or flexible cables for incorporation in space challenged applications. In particular, the present invention relates to methods and apparatus for the assembly and construction of conducting elements for electrical attachment such as connecting to sensors along the body of the guidewire.

BACKGROUND OF THE INVENTION

Guidewires may have a number of sensors or sensor assemblies integrated directly into the guidewire. Such sensor-equipped guidewires may be adapted for measuring various parameters within a patient's body. Sensors typically have one or more cables passed through the guidewire for electrically coupling the sensor element to an electronic assembly that is placed outside the patient body.

Guidewires are generally comprised of a hypotube or a solid core segment and coiled segment about a core wire which may extend through the length or a partial length of the guidewire. The core wire may be fabricated from stainless steel or Nitinol with the coiled segment fabricated from a wire or braid which provide for flexibility, pushability, and kink resistance to the guidewire. Nitinol wire, used by itself or braided with stainless steel, may further help to increase flexibility and allow the wire to spring back into shape.

Moreover, guidewires have a standard diameter of 0.014 inch (about 0.3 mm) and accommodating certain types of sensors or having multiple sensors may be limited by the relatively small space provided by the guidewire. Moreover, guidewires are typically used for insertion into and advancement through the vasculature which can present an extremely tortuous pathway. Therefore, the guidewire has to be optimized for having the best mechanical performance needing a construction closer to the conventional guidewires with core wire. This further put limitation on space. In addition, if conventional conducting elements are used, the stress generated due to flexing may cause shifts in the relative position of conductors giving rise to change in electrical coupling. Additionally, having a guidewire passing through different environments (such as a blood-filled environment within the vessels and the environment external to the patient's body) may cause electrical instability within any conducting wires which pass through the length of the guidewire. Such challenges may cause undesired artifacts in measurements thus affecting sensor performance.

Guidewires incorporating one or more electrodes along their length may present additional challenges to guidewire construction and use. For instance, the presence of a plurality of electrodes along the guidewire may require additional conductive wiring passed through the length of the guidewire. Because of the limited space and flexibility required from guidewires, any sensors and/or electrodes positioned along their length are desirably correspondingly constructed.

Consequently, there is a need to design conducting elements that take up minimal space, can be long or short depending on the need, have limited changes in electrical network during operation and offer most manufacturing and process flexibility to accommodate connections to a multitude of sensing elements.

SUMMARY OF THE INVENTION

Guidewires which are configured to sense or detect parameters within a patient body may be fabricated through a combination of various methods (e.g., chemical milling, lamination of coverlays, laser cutting, etc.) which can accommodate the micron-level electrical assemblies while still maintaining electrical stability throughout the length of the guidewire or instrument. The conductive wires which extend through the guidewire may be fabricated in a manner which enables the electrical coupling to micron-scale connections and which also provides electrical stability to the signals passing through the conductive wires.

Generally, one method of forming such a conductive wire may comprise forming one or more conductive elements along a first direction upon an insulative substrate, forming an insulative coverlay upon the one or more conductive elements, selectively forming at least one opening or window through the insulative coverlay to expose a portion of the one or more conductive elements, forming a conductive coating upon the insulative coverlay such that the conductive coating is in contact with the portion of the one or more conductive elements through the at least one opening or window, and removing at least one region of the conductive coating along a second direction in proximity to the at least one opening or window such that one or more conductive pads are formed and are electrically isolated from a remainder of the conductive coating.

Such a conductive wire assembly may generally comprise an insulative substrate having a length, one or more conductive elements formed along a first direction upon the substrate, an insulative coverlay formed upon the one or more conductive elements, at least one opening or window defined through the insulative coverlay exposing a portion of the one or more conductive elements, a conductive coating formed upon the insulative coverlay such that the conductive coating is in contact with the portion of the one or more conductive elements through the at least one opening or window, and wherein the conductive coating has at least one region removed along a second direction in proximity to the at least one opening or window such that one or more conductive pads are formed and are electrically isolated from a remainder of the conductive coating.

One variation may include a multi-strand flat wire with conductive wires (e.g., copper or other conductive material) having a diameter of, e.g., 0.0014 inch, which are individually insulated by corresponding layers of insulation (e.g., polyimide). These individual insulated wires may be bonded together, e.g., via polyimide, butryl, or other adhesive) such that the wires are aligned as a flat wire. The distal portion and proximal portion of the flat wire may have portions of the insulative layer ablated (e.g., etching, laser ablation, etc.) to form windows or openings along the distal portion and windows or openings along the proximal portion to expose the underlying conductive wires. These windows or openings may be formed so that they are staggered relative to one another along the length of the flat wire to provide sufficient spacing between the windows or openings for connection to sensors or other components.

Because the flat wire may be routed along the length of the guidewire or instrument, the flat wire is desirably electrically stable as signals pass through the length of the wire. As the guidewire or instrument may extend in use from sensors positioned within an aqueous environment (such as within a blood-filled environment within the patient body) to an environment external to the patient body such as a surgical suite or operating room, the transmission of signals through the wire may be electrically stabilized by coating the length of the wire by a conductive material such as metal (e.g., copper, palladium, gold, aluminum, etc.) which may be applied, e.g., via vapor deposition or electro-less coating methods. Application of such a conductive material makes the conducting elements housed within a constant network which is agnostic to the outside environment. For example, having a conductive saline medium versus a de-ionized water or air medium will not affect the electrical network between the distal and proximal ends of the conducting element.

This metal coating may fill in the individual windows or openings along both the distal and proximal portions. However, to prevent shorting of any electrical signals, the portions just proximal and distal to each of the windows or openings may be etched in a transverse direction relative to the length of the wire to form non-conductive barriers between adjacent windows or openings. These regions form electrically isolated pads which are electrically coupled to the respective conductive wires exposed through their respective windows or openings along both the distal and proximal portions. Because these isolated pads are also enlarged relative to the window or opening, electrically coupling sensors or other devices to individual conductive wires is greatly facilitated along both distal and proximal portions.

The flat wire assembly may be used to form flex circuit assemblies by taking an inverted flat wire and electrically coupling the exposed windows or openings to another flat wire having corresponding exposed windows or openings.

In another variation, rather than using individually insulated conducting wires, conductive traces (e.g., gold, nickel, copper, etc.) having a thickness of, e.g., 0.0005 inch to 0.002 inch, and a width of, e.g., 0.001 inch, may be electrodeposited upon an insulative substrate such as a polyimide film (e.g., Kapton®, E. I. du Pont de Nemours) having a thickness of, e.g., 0.0005 inch to 0.002 inch. The traces may be aligned to have a gap between adjacent traces of, e.g., 0.001 inch or more, and a second insulative layer coverlay such as another polyimide film (e.g., Kapton®) may be overlaid upon the traces such that the traces are sandwiched between the substrate and coverlay. These traces may be deposited upon the substrate either through an additive process or subtractive process (e.g., etching, milling, etc.) where the substrate may be initially surface-treated and cured prior to having the traces deposited upon the substrate using a suitable photo-imaging mask to the desired height and width. Once the coverlay has been deposited over the traces, the appropriate window or opening, as described herein, may be etched or ablated over the desired portion of each trace to create the staggered openings along the length of the flat wire.

Additionally, a metal coating may be further deposited upon the length of the resulting flex wire and the appropriate window or opening may be formed to create a larger surface area for electrically connecting to other elements. The coating may be deposited via a process such as vapor deposition.

Rather than having each of the traces aligned along a first or upper surface of the substrate, the traces may also be positioned along a second or lower surface of the substrate as well. While the upper surface has coverlay, the lower surface may also have a coverlay deposited upon the traces although either one or both coverlay may be optionally omitted. The traces may be positioned to be aligned directly in apposition to one another while another variation may have the traces aligned in an alternating pattern relative to one another while on respective upper and lower surfaces. In yet another variation, the traces may be aligned at a first distance from one another while the traces may be aligned at a second distance from one another where the traces on the lower surface are closer relative to the traces on the upper surface.

Because the traces may be formed into a wire extending over a distance, e.g., 72 inches or more, the traces may be formed (e.g., photo-etched) upon the substrate in a circular spiral pattern with connection pads formed on either end of the traces for distal and proximal connections. The traces may be arranged in the circular spiral pattern to allow for the packing of a long flex cable in a relatively small footprint.

A laser such as a femto-second laser may be used for singulation or an instrument such as a slitter tool (blade or roller type) may be used. An optical system may be used to track the traces and correct the slitter (or laser) path through a feedback control system. In another variation, one of the conducting traces can be used a sacrificial trace used for cutting. This may be done by injecting calculated amount of electric current that causes the conducting element to heat up beyond the glass transition temperature of the base and coverlay polymer. A slight amount of lateral pressure can be used simultaneously to form the cut. One advantage of this method would be that the trace is self-aligning potentially obviating the need for a closed loop feedback vision system. It is also noted that the holding down of the part in a precise location is desirable as a slight misalignment can lead to the cutting elements (slitter or laser) to travel into one of the traces and destroy the part. The parts may be made with fiducials that help the cutting tools to make initial alignment. Additionally, when the cutting progresses the part may have a tendency to lift off or warp locally. One method to prevent this is by using a porous vacuum chuck and another method is to mount the part on a gel pack (or similar adhesive backed surface) that keeps the part from lifting off locally. Yet another method that can be used in a laser cutting operation is to sandwich the part between two sheets of glass.

Depending up the application in which the wire is used, the length of the flex needed can vary between, e.g., 78 inches to 118 inches, depending on the length of the guidewire. There can be tooling or process limitations of getting a flex of that length. In such cases a hybrid approach may be useful where short flexes are used on both ends and these are connected to conductors. The flex pads offer the flexibility and versatility of size and configuration of pads and circuitry appropriate to the application (e.g., to attach to a corresponding pads of a MEMS sensor). The conductor wires allow the use of mass manufacturing processes.

In another variation, the conductive traces may be formed as a waveguide having active traces and ground traces arranged in various configurations. In yet another variation, the assembly may be formed for connection to multiple sensors. In another variation, each of the active traces may be aligned along the upper surface and the sensor traces may be aligned along the lower surface such that the active and sensor traces are arranged in an alternating pattern.

With the electrical traces or flat wire formed, the assembly may then be integrated within a guidewire assembly. In one method, the flat wire or flex wire assembly may be attached to a core wire such that the distal pad assembly is aligned near or at distal end of the core wire, e.g., along the reduced distal section of the core wire such that the exposed pads face away from the surface of the distal section. The traces or wires extending from the distal pad assembly may be wound or wrapped around the core. Conductive ring elements may be positioned over the distal section of the core wire and over the distal pad assembly such that each ring element corresponds to each conductive pads along the distal pad assembly. The ring elements may be soldered or otherwise attached via a conductive adhesive (such as conductive epoxy) such that each ring element is in electrical communication with each respective conductive pad. The ring elements may be made of any metal or conductive material and may serve as an electrode terminal exposed along the guidewire surface. With the ring elements desirably positioned and attached along the distal section, an electrically insulative polymer may be reflowed or molded in-between the ring elements and the resulting electrode assembly may be sized (e.g., via center-less grinding, laser ablation, etc.) to yield a seamless transition between the ring surface and polymer to produce an electrode assembly upon the guidewire.

In another variation, rather than utilizing an electrically insulative polymer, pre-cut and pre-sized polymeric spacers may be positioned upon the distal section in-between each of the ring elements to electrically isolate the resulting electrodes.

In yet another variation, rather than forming the electrode assembly directly upon the core wire, an electrode subassembly may be assembled separately and then attached to the core wire. In this variation, the base tube may also include the polymeric spacers positioned and secured between the adjacent ring elements. Alternatively, the electrode subassembly, may be similarly formed but without the polymeric spacers.

In either case, the electrode subassembly may be positioned collinearly at the distal end of the distal section of the core wire such that the distal end of the core wire is in direct apposition with the proximal end of the electrode subassembly. A collar (e.g., stainless steel, nitinol, etc.) may be positioned to surround the distal section of core wire and the proximal section of the subassembly such that the interface between distal section and proximal end is contained within the collar. The traces or wires extending from the subassembly may be passed through the interior of collar and secured around the core wire. This interface, as well as the portions of the distal section and subassembly may be secured within the collar through any number of mechanisms, e.g., solder, adhesive, crimping, etc., such that the core wire and subassembly are joined to one another in a secure manner.

With the subassembly joined to the core wire, the portions between the adjacent ring members may be filled with a reflowed or molded polymer to electrically isolate the adjacent electrodes from one another. In the event that subassembly having the polymeric spacers is used, the attachment between the core wire and subassembly may be made without having to reflow any polymer. Using either subassembly, the subassembly (and core wire) may be sized (e.g., grinding, laser ablation, etc.) to ensure that the transition between the two assemblies is flush and seamless.

BRIEF DESCRIPTION OF THE DRAWINGS

FIGS. 1A and 1B show cross-sectional end and top views of a multi-strand flat wire.

FIG. 2A shows a top view of the flat wire having portions of the insulation etched to expose the conducting wires.

FIG. 2B shows the top view of the flat wire with a metal coating disposed upon the wire.

FIGS. 7A and 7B show top views of another variation for arranging the distal terminal ends of the conductive elements and the traces or wires upon a substrate.

FIGS. 8A and 8B show end views of a spiral pattern into which the conductive traces or wires may be configured.

DETAILED DESCRIPTION OF THE INVENTION

Figure 3A:
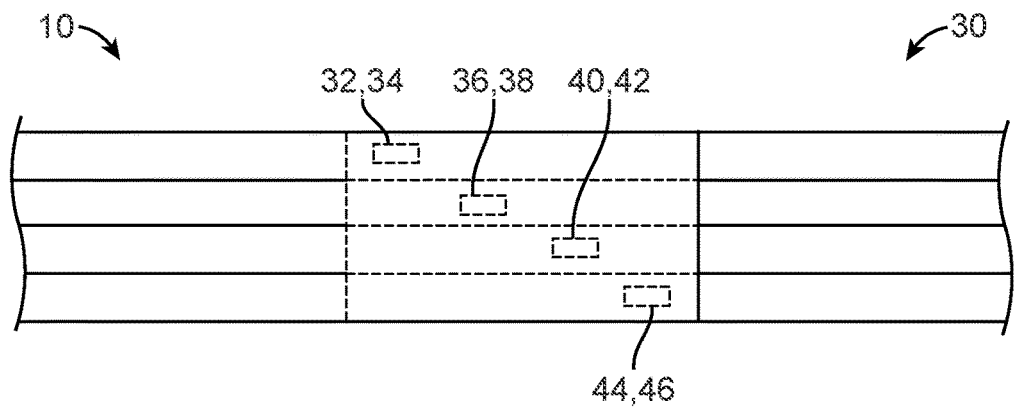
FIGS. 3A and 3B show top and side views of two multi-strand flat wires which are electrically coupled to one another through the exposed openings.

In assembling guidewires which are configured to sense or detect parameters within a patient body, the guidewire assemblies may be fabricated through a combination of various methods (e.g., chemical milling, lamination of coverlays, laser cutting, etc.) which can accommodate the micron-level assemblies while still maintaining electrical stability throughout the length of the guidewire or instrument. Examples of guidewire instruments which may utilize such assemblies may include a combination intravascular fractional flow resistance (FFR) and cross-sectional area (CSA) measurement instrument utilizing via multi-frequency electrical excitation via a guidewire as shown and described in further detail in U.S. Pat. Nos. 8,798,712; 8,374,689; 8,494,794; 8,825,151; U.S. Pat. Pubs. 2013/0123694; 2014/0142398; and U.S. patent application Ser. Nos. 14/535,165; and 14/535,204. Each of these references is incorporated herein by reference in its entirety and for any purpose.

One variation is illustrated in the cross-sectional end and top views of FIGS. 1A and 1B which show an exemplary multi-strand flat wire 10 having conductive wires 12A, 12B, 12C, 12D (e.g., copper or other conductive material) having a diameter of, e.g., 0.0014 inch, which may be individually insulated by corresponding layers of insulation 14A, 14B, 14C, 14D (e.g., polyimide). These individual insulated wires may be bonded together, e.g., via polyimide, butryl, or other adhesive) such that the wires are aligned as a flat wire as shown. As shown in the top view of FIG. 2A, the distal portion 16 and proximal portion 18 of the flat wire 10 may have portions of the insulative layer ablated (e.g., etching, laser ablation, etc.) to form windows or openings 20A, 20B, 20C, 20D along the distal portion 16 and windows or openings 22A, 22B, 22C, 22D along the proximal portion 18 to expose the underlying conductive wires. These windows or openings may be formed so that they are staggered relative to one another along the length of the flat wire 10 to provide sufficient spacing between the windows or openings for connection to sensors or other components.

Because the flat wire 10 may be routed along the length of the guidewire or instrument, the flat wire 10 is desirably electrically stable as signals pass through the length of the wire 10. As the guidewire or instrument may extend in use from sensors positioned within an aqueous environment (such as within a blood-filled environment within the patient body) to an environment external to the patient body such as a surgical suite or operating room, the transmission of signals through the wire 10 may be electrically stabilized by coating the length of the wire 10 by a conductive material such as metal (e.g., copper, palladium, gold, aluminum, etc.) which may be applied, e.g., via vapor deposition or electroless coating methods. Application of such a conductive material makes the conducting elements housed within a constant network which is agnostic to the outside environment. For example, having a conductive saline medium versus a de-ionized water or air medium will not affect the electrical network between the distal and proximal ends of the conducting element.

FIG. 2B shows a top view of the wire 10 coated along its length from the distal portion 16 to the proximal portion 18 by a metal coating 24. This metal coating 24 may also fill in the individual windows or openings along both the distal and proximal portions 16, 18. However, to prevent shorting of any electrical signals, the portions just proximal and distal to each of the windows or openings may be etched in a second direction (e.g., transverse) relative to the length of the wire 10 to form non-conductive barriers 26 between adjacent windows or openings. These regions form electrically isolated pads which are electrically coupled to the respective conductive wires 12A, 12B, 12C, 12D exposed through their respective windows or openings along both the distal and proximal portions 16, 18. Because these isolated pads are also enlarged relative to the window or opening, electrically coupling sensors or other devices to individual conductive wires is greatly facilitated along both distal and proximal portions 16, 18.

Figure 3B:
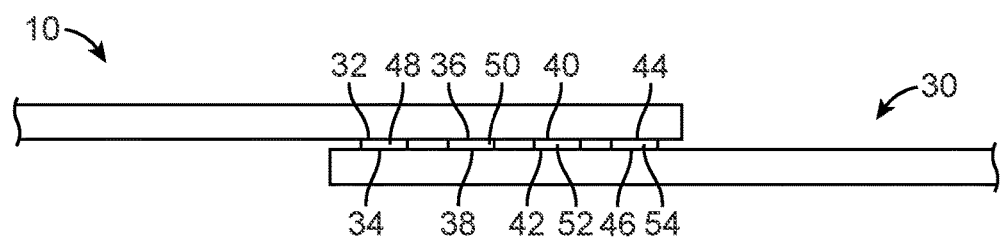

The flat wire 10 assembly may be used to form flex circuit assemblies by taking an inverted flat wire 10 and electrically coupling the exposed windows or openings to another flat wire 30 having corresponding exposed windows or openings. An example is shown in the top and side views of FIGS. 3A and 3B which show an inverted flat wire 10 having staggered windows or openings 32, 36, 40, 44 aligned with correspondingly staggered windows or openings 34, 38, 42, 46 along flat wire 30. Solder 48, 50, 52, 54 may be flowed between the corresponding windows or openings to create an electrical connection between individual conductive wires. Alternatively, a material such as conductive epoxy may be dispensed upon the ablated portions of the wires and then cured using heat. Precuring adhesive on the wires may create a pad-like surface to help accommodate any alignment errors and to alleviate any assembly challenges. Furthermore, curing the adhesive may effect positive electrical contact.

In another variation, rather than using individually insulated conducting wires, conductive traces 34 (e.g., gold, nickel, copper, etc.) having a thickness of, e.g., 0.0005 inch to 0.002 inch, and a width of, e.g., 0.001 inch, may be electro-deposited upon an insulative substrate 32 such as a polyimide film (e.g., Kapton®, E. I. du Pont de Nemours) having a thickness of, e.g., 0.0005 inch to 0.002 inch, as shown in the cross-sectional end view of FIG. 4 which illustrates four traces 34 aligned adjacent to one another to form a flex wire assembly. The traces 34 may be aligned to have a gap between adjacent traces of, e.g., 0.001 inch or more, and a second insulative layer coverlay 36 such as another polyimide film (e.g., Kapton®) may be overlaid upon the traces 34 such that the traces 34 are sandwiched between the substrate 32 and coverlay 36. These traces 34 may be deposited upon the substrate 32 either through an additive process or subtractive process (e.g., etching, milling, etc.) where the substrate 32 may be initially surface-treated and cured prior to having the traces 34 deposited upon the substrate 32 using a suitable photo-imaging mask to the desired height and width. Once the coverlay 36 has been deposited over the traces 34, the appropriate window or opening, as previously described, may be etched or ablated over the desired portion of each trace 34 to create the staggered openings along the length of the flat wire (as shown above in FIG. 2A).

Additionally, a metal coating 24 may be further deposited upon the length of the resulting flex wire and the appropriate window or opening may be formed (as shown above in FIG. 2B) to create a larger surface area for electrically connecting to other elements. The coating 24 may be deposited via a process such as vapor deposition.

Figure 4:
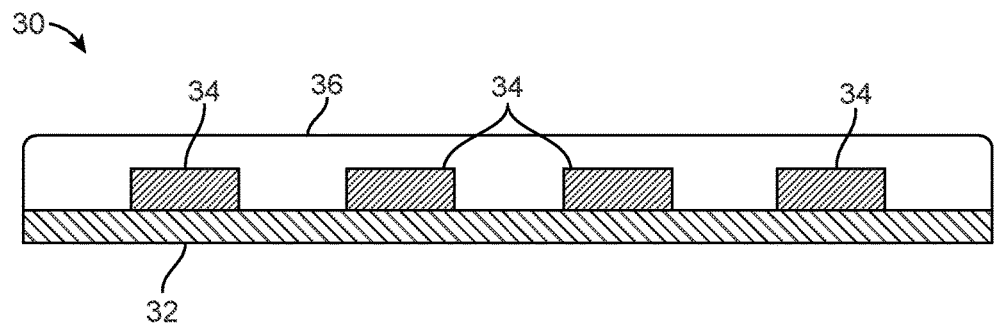
FIG. 4 shows a cross-sectional end view of one variation of conductive traces or wires layered between insulating layers.
Figure 5A:
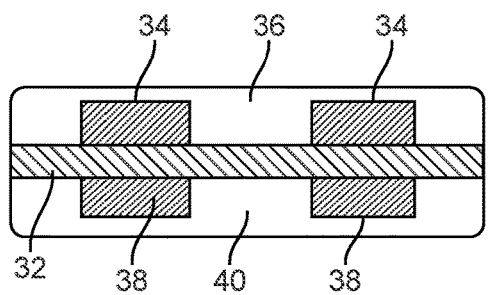
FIGS. 5A to 5C show cross-sectional end views of alternative variations for arranging the conductive traces or wires.
Figure 5B:
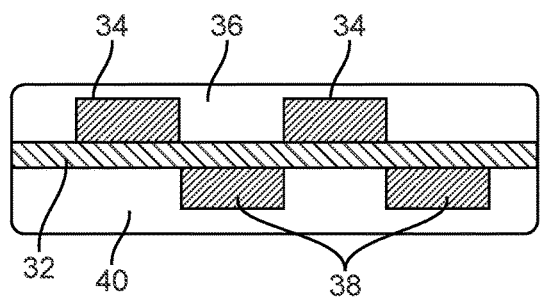
Figure 5C:
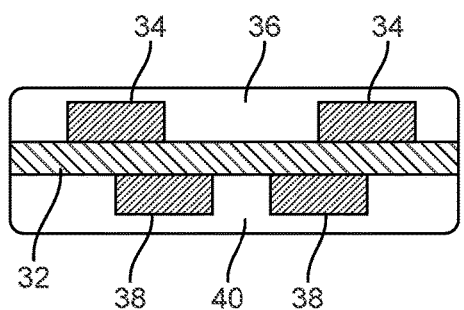

Rather than having each of the traces 34 aligned along a first or upper surface of the substrate 32, as shown in FIG. 4, the traces 34 may also be positioned along a second or lower surface of the substrate 32 as well. FIG. 5A shows a cross-sectional end view where two traces 34 are aligned upon the upper surface of substrate 32 while two additional traces 38 are aligned upon the lower surface of substrate 32. While the upper surface has coverlay 36, the lower surface may also have a coverlay 40 deposited upon the traces 38 although either one or both coverlay 36, 40 may be optionally omitted. In this variation, the traces 34 and 38 are positioned to be aligned directly in apposition to one another while another variation, as shown in FIG. 5B, may have the traces 34 and 38 aligned in an alternating pattern relative to one another while on respective upper and lower surfaces. In yet another variation as shown in FIG. 5C, the traces 34 may be aligned at a first distance from one another while the traces 38 may be aligned at a second distance from one another where the traces 38 on the lower surface are closer relative to the traces 34 on the upper surface.

Figure 6A:
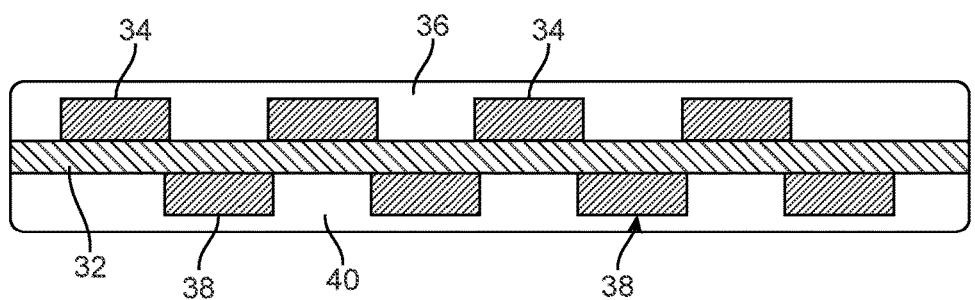
FIGS. 6A and 6B show cross-sectional end views of alternative variations for arranging multiple conductive traces or wires, e.g., eight traces or wires.
Figure 6B:
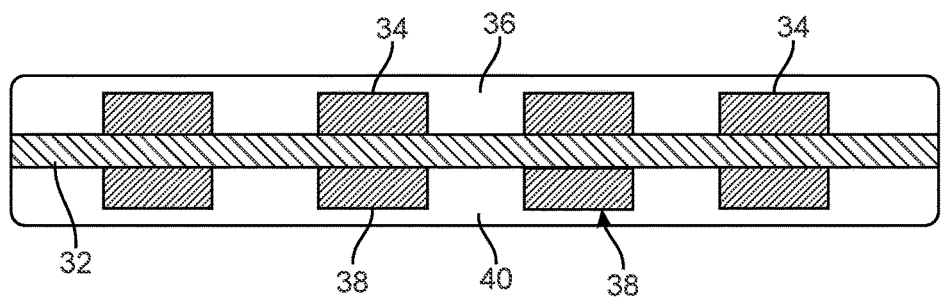

In yet another variation, FIG. 6A shows a cross-sectional end view of a substrate 32 having additional traces 34 along the upper surface (e.g., total of four traces 34) and additional traces 38 along the lower surface (e.g., total of four traces 38) where the traces 34 and 38 are aligned in an alternating and staggered pattern. FIG. 6B shows a cross-sectional end view where each of the traces 34 and 38 are aligned in apposition to one another along respective upper and lower surfaces. While a total of eight traces are shown, the number of traces along the upper surface and/or lower surface may be varied in any number of combinations and positions to accommodate the desired electrical configuration and application.

Because the traces may be formed into a wire extending over a distance, e.g., 72 inches or more, the traces may be formed (e.g., photo-etched) upon the substrate 50 in a circular spiral pattern 60 with connection pads formed on either end of the traces for distal and proximal connections. The traces may be arranged in the circular spiral pattern 60 to allow for the packing of a long flex cable in a relatively small footprint. FIG. 7A shows an example where individual traces 52, 54, 56, 58 may are formed upon the substrate 50 and extend to corresponding pads 1d, 2d, 3d, 4d staggered longitudinally relative to one another. FIG. 7B shows an example of how the individual traces 64 may be aligned in parallel while arranged in a circular pattern upon the substrate 62. These individual traces may be singulated to form a viable flex cable or wire, i.e., the individual traces may be singled out to form into a flex circuit element, as described above.

FIGS. 8A and 8B show top views of a flex circuit trace print removed from the substrate where the traces are arranged in the circular spiral pattern 60. A laser such as a femto-second laser may be used for singulation or an instrument such as a slitter tool (blade or roller type) may be used. An optical system may be used to track the traces and correct the slitter (or laser) path through a feedback control system. In another variation, one of the conducting traces can be used a sacrificial trace used for cutting. This may be done by injecting calculated amount of electric current that causes the conducting element to heat up beyond the glass transition temperature of the base and coverlay polymer. A slight amount of lateral pressure can be used simultaneously to form the cut. One advantage of this method would be that the trace is self-aligning potentially obviating the need for a closed loop feedback vision system. It is also noted that the holding down of the part in a precise location is desirable as a slight misalignment can lead to the cutting elements (slitter or laser) to travel into one of the traces and destroy the part. The parts may be made with fiducials that help the cutting tools to make initial alignment. Additionally, when the cutting progresses the part may have a tendency to lift off or warp locally. One method to prevent this is by using a porous vacuum chuck and another method is to mount the part on a gel pack (or similar adhesive backed surface) that keeps the part from lifting off locally. Yet another method that can be used in a laser cutting operation is to sandwich the part between two sheets of glass.

The terminal distal end and proximal end of the traces are shown extending in their respective pads 1d, 2d, 3d, 4d and 1p, 2p, 3p, 4p. An additional pad 5p at the proximal end is shown as a floating pad. In applications where multiple conductors are desired but have to be packed in a tight space, dual clad traces may be laid out, as described above. This may be particularly advantageous when the sensors can be longitudinally displaced.

Depending up the application in which the wire is used, the length of the flex needed can vary between, e.g., 78 inches to 118 inches, depending on the length of the guidewire. There can be tooling or process limitations of getting a flex of that length. In such cases a hybrid approach may be useful where short flexes are used on both ends and these are connected to conductors. The flex pads offer the flexibility and versatility of size and configuration of pads and circuitry appropriate to the application (e.g., to attach to a corresponding pads of a MEMS sensor). The conductor wires allow the use of mass manufacturing processes.

Figure 9A:
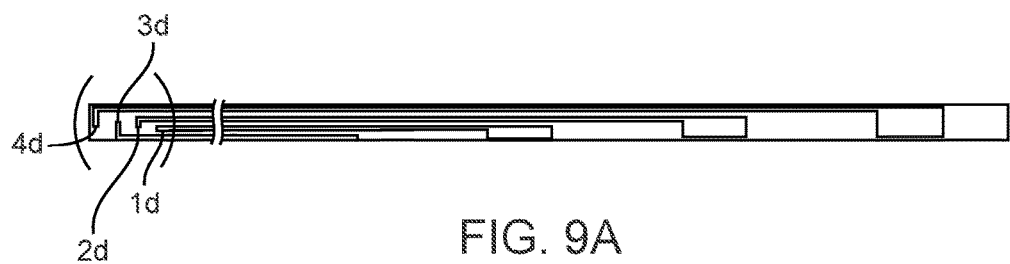
FIGS. 9A and 9B show top and detail views of another variation for arranging the conductive traces or wires.
Figure 9B:
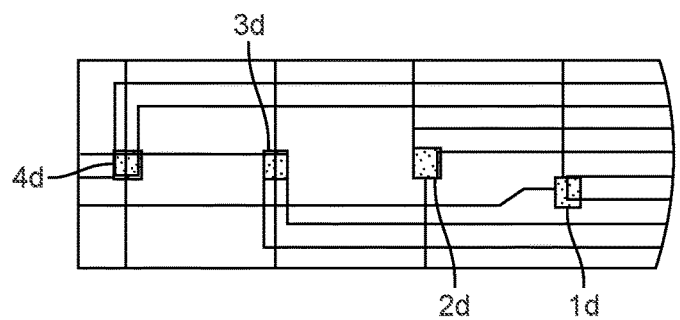
Figure 9C:
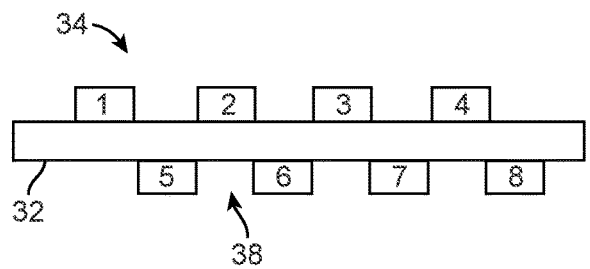
FIGS. 9C to 9E show cross-sectional end and top views illustrating another variation for arranging multiple conductive traces or wires.
Figure 9D:
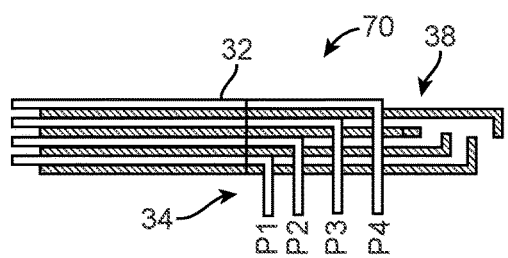
Figure 9E:

As shown in the top and detail views of FIGS. 9A and 9B, an example is shown of the distal pads 1d, 2d, 3d, 4d may be aligned relative to one another such that the pads are longitudinally spaced apart along the wire. While the variation shown may accommodate four individual traces (or wires aligned on the same surface of the substrate, FIGS. 9C to 9E show cross-sectional end and top views of another variation of an assembly which may accommodate multiple traces 34 (e.g., four traces) along an upper surface of substrate 32 and multiple traces 38 (e.g., four traces) along a lower surface of substrate 32, as previously described. The traces 34, 38 may be correspondingly spaced along the distal portion 70 and proximal portion 72 of the assembly such that the traces may be longitudinally aligned on either the upper or lower surface for electrical connection to multiple sensors or components.

Figure 10A:
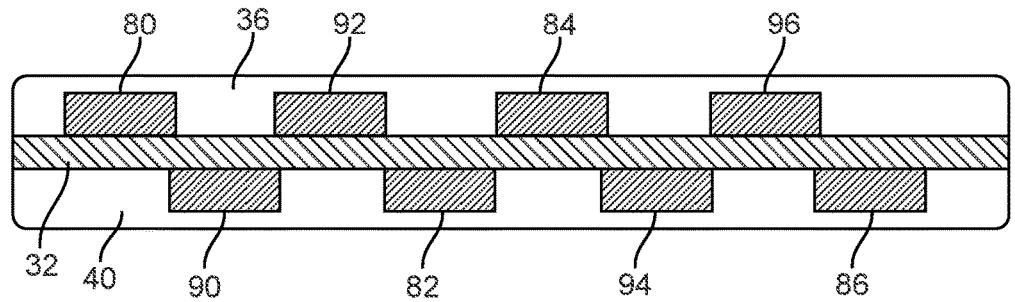
FIGS. 10A and 10B show cross-sectional end views of another variation for configuring a wave guide of conductive traces or wires with respect to ground traces or wires.
Figure 10B:
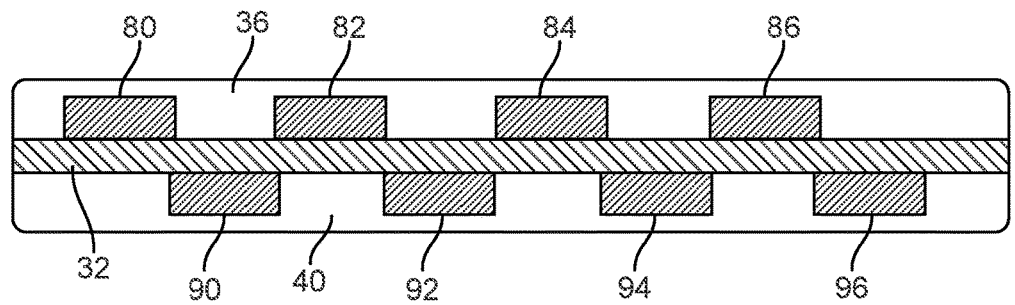

As described above, the traces may be formed along either or both of the upper and/or lower surfaces of the substrate 32. In another variation, the conductive traces may be formed as a waveguide having active traces and ground traces arranged in various configurations. FIG. 10A shows a cross-sectional end view of one variation where the active traces 80, 82, 84, 86 may be aligned in a staggered arrangement over both the upper and lower surfaces of substrate 32 with ground traces 90, 92, 94, 96 interspersed in an alternating pattern between the adjacent active traces 80, 82, 84, 86. Each of the upper and lower surfaces may be overlaid with coverlay 36, 40. FIG. 10B shows another variation where the active traces 80, 82, 84, 86 may be aligned along the upper surface of substrate 32 while each of the ground traces 90, 92, 94, 96 may be aligned along the lower surface while staggered relative to the active traces on the upper surface.

Figure 11A:
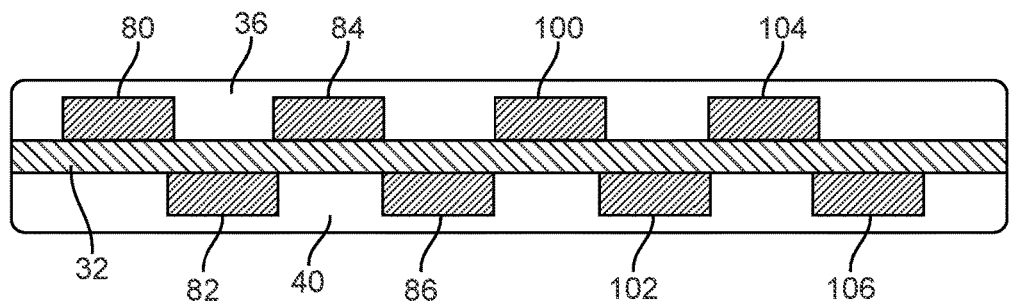
FIGS. 11A and 11B show cross-sectional end views of another variation for configuring multiple traces or wires for a multi-sensor connection.

In yet another variation, the assembly may be formed for connection to multiple sensors. FIG. 11A shows one variation in a cross-sectional end view where active traces 80, 84 may be aligned on the upper surface and active traces 82, 86 may be aligned on the lower surface of substrate 32 such that these active traces are aligned alternatingly relative to a first edge of the substrate 32. The sensor traces 100, 104 may be aligned on the upper surface adjacent to one another while sensor traces 102, 106 may be aligned on the lower surface adjacent to another such that these sensor traces are aligned alternatingly relative to a second edge of the substrate 32 which is opposite to the first edge.

Figure 11B:
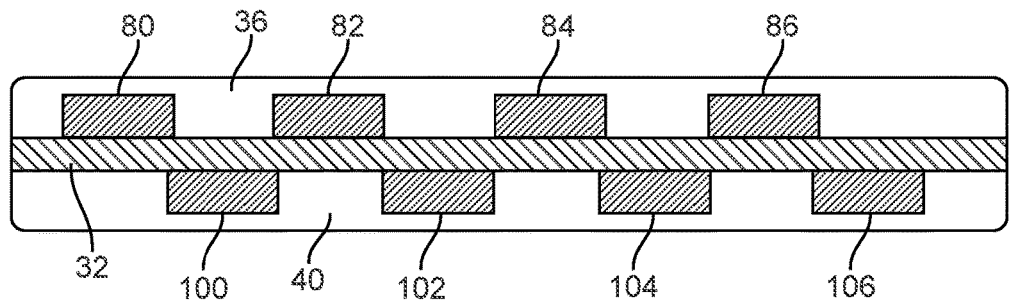

In another variation as shown in the cross-sectional end view of FIG. 11B, each of the active traces 80, 82, 84, 86 may be aligned along the upper surface and the sensor traces 100, 102, 104, 106 may be aligned along the lower surface such that the active and sensor traces are arranged in an alternating pattern.

Figure 12A:
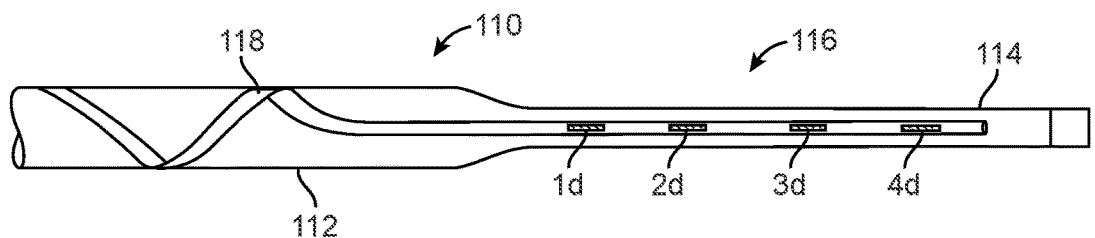
FIGS. 12A to 12D show top views of one example for attaching conductive traces or wires to a core wire for forming an electrode assembly.
Figure 12B:
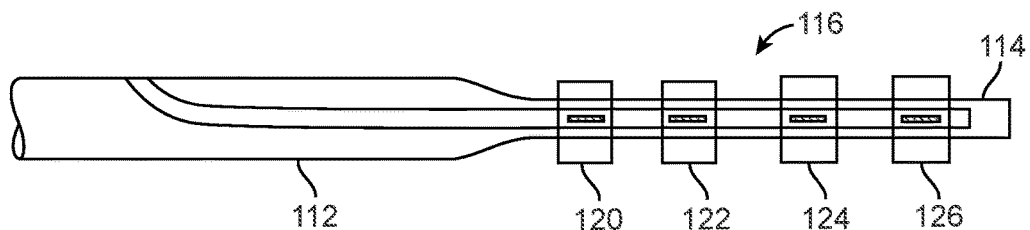
Figure 12C:
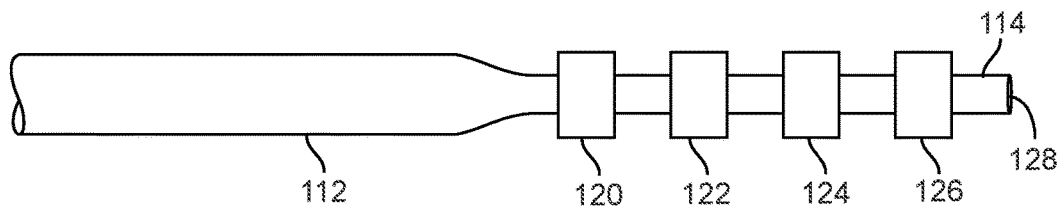

With the electrical traces or flat wire formed, the assembly may then be integrated within a guidewire assembly. In one method, the flat wire or flex wire assembly may be attached to a core wire 110 such that the distal pad assembly 116 is aligned near or at distal end of the core wire 110, e.g., along the reduced distal section 114 of the core wire 110 such that the exposed pads face away from the surface of the distal section 114. The traces or wires 118 extending from the distal pad assembly 116 may be wound or wrapped around the core 112, as shown in the side view of FIG. 12A. Conductive ring elements 120, 122, 124, 126 may be positioned over the distal section 114 of the core wire 110 and over the distal pad assembly 116 such that each ring element 120, 122, 124, 126 corresponds to each conductive pads 1d, 2d, 3d, 4d along the distal pad assembly 116, as shown in FIG. 12B. The ring elements may be soldered or otherwise attached via a conductive adhesive (such as conductive epoxy) such that each ring element is in electrical communication with each respective conductive pad, as shown in FIG. 12C. The ring elements may be formed to maintain distances between adjacent ring elements to within 50 μm accuracy. The distance between each ring element may be uniform or arbitrary or they may be set at specified distances. For instance, the distance between ring element 120 and 122 may be set at, e.g., 1.6 mm, the distance between ring element 122 and 124 may be set at, e.g., 1.3 mm, and the distance between ring element 124 and 126 may be set at, e.g., 1 mm.

Figure 12D:
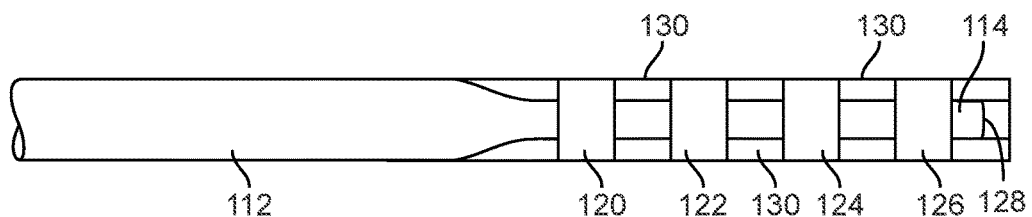

The ring elements 120, 122, 124, 126 may be made of any metal or conductive material and may serve as an electrode terminal exposed along the guidewire surface. The end 128 of the distal section 114 may also be cut to length depending upon the desired length of the core wire 110. With the ring elements desirably positioned and attached along the distal section 114, an electrically insulative polymer 130 may be reflowed or molded in-between the ring elements 120, 122, 124, 126 and the resulting electrode assembly may be sized (e.g., via center-less grinding, laser ablation, etc.) to yield a seamless transition between the ring surface and polymer 130 to produce an electrode assembly upon the guidewire, as shown in FIG. 12D.

Figure 13A:
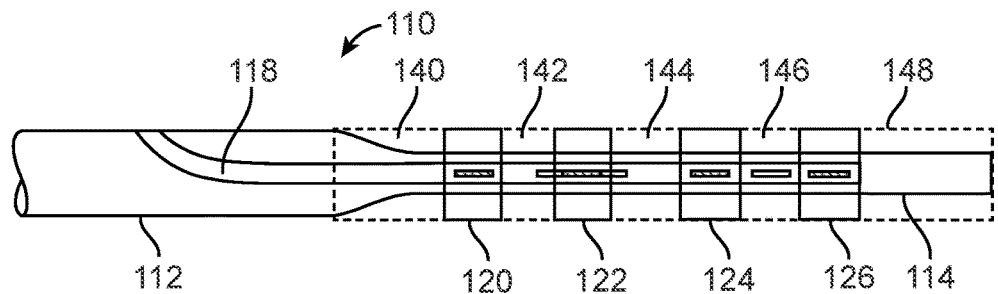
FIG. 13A shows a top view of another variation of an electrode assembly having spaces positioned between the conductive pads.

In another variation, rather than utilizing an electrically insulative polymer 130, pre-cut and pre-sized polymeric spacers 140, 142, 144, 146, 148 may be positioned upon the distal section 114 in-between each of the ring elements 120, 122, 124, 126 to electrically isolate the resulting electrodes, as shown in the side view of FIG. 13A.

Figure 13B:
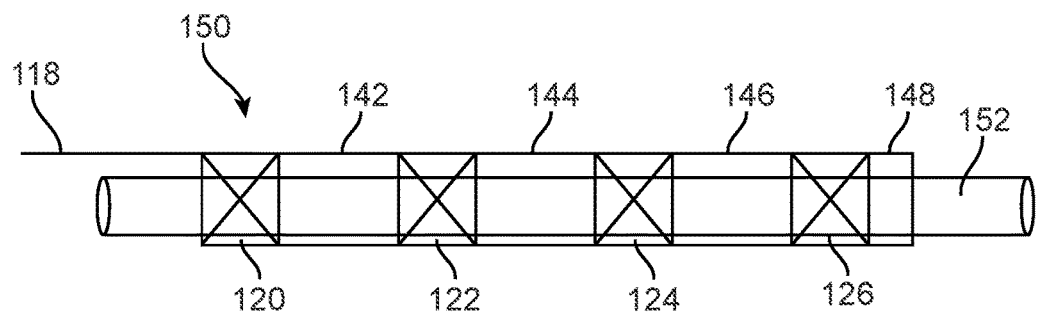
FIGS. 13B and 13C show top views of another variation of electrode subassemblies which may be assembled and coupled to a core wire.
Figure 13C:
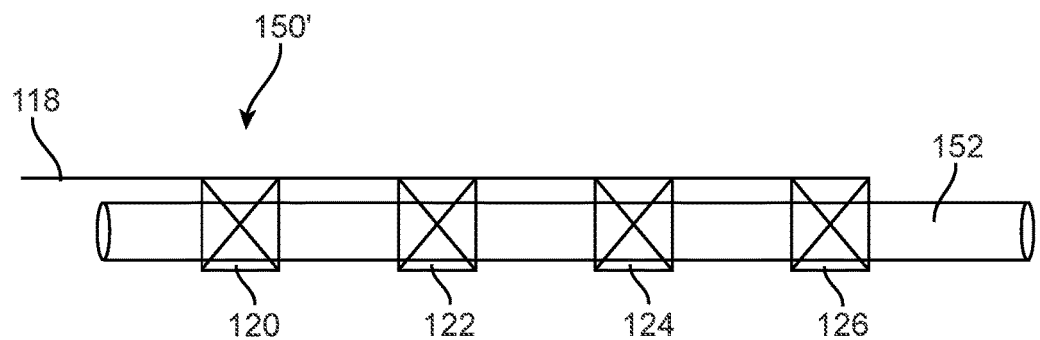

In yet another variation, rather than forming the electrode assembly directly upon the core wire, an electrode subassembly 150 may be assembled separately and then attached to the core wire. FIG. 13B shows a side view of one variation where a separate base tube 152 (e.g., polyimide or other polymer, insulated metal, etc.) may be formed with the distal pad assembly 116 and ring elements 120, 122, 124, 126, as previously described. Traces or wires 118 may be seen extending from the distal pad assembly 116 located within the ring elements. In this variation, base tube 152 may also include the polymeric spacers 142, 144, 146, 148 positioned and secured between the adjacent ring elements. Alternatively, electrode subassembly 150', as shown in the side view of FIG. 13C, may be similarly formed but without the polymeric spacers.

Figure 14A:
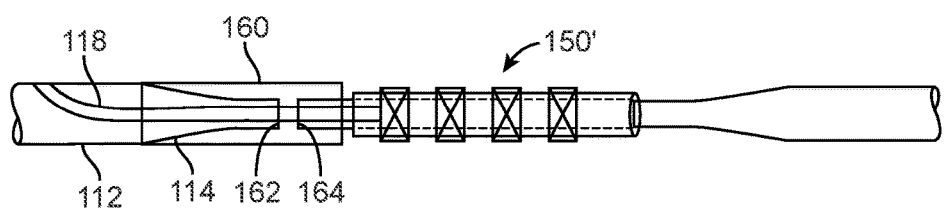
FIGS. 14A to 14C show top views illustrating variations for coupling electrode subassemblies to a core wire.

In either case, the electrode subassembly 150' may be positioned collinearly at the distal end of the distal section 114 of core wire 112 such that the distal end 162 of core wire 112 is in direct apposition with the proximal end 164 of electrode subassembly 150', as shown in the side view of FIG. 14A. A collar 160 (e.g., stainless steel, nitinol, etc.) may be positioned to surround the distal section 114 of core wire 112 and the proximal section of subassembly 150' such that the interface between distal section 114 and proximal end 162 is contained within the collar 160. The traces or wires 118 extending from subassembly 150' may be passed through the interior of collar 160 and secured around the core wire 112. This interface, as well as the portions of the distal section 114 and subassembly 150' may be secured within the collar 160 through any number of mechanisms, e.g., solder, adhesive, crimping, etc., such that the core wire 112 and subassembly 150' are joined to one another in a secure manner.

Figure 14B:
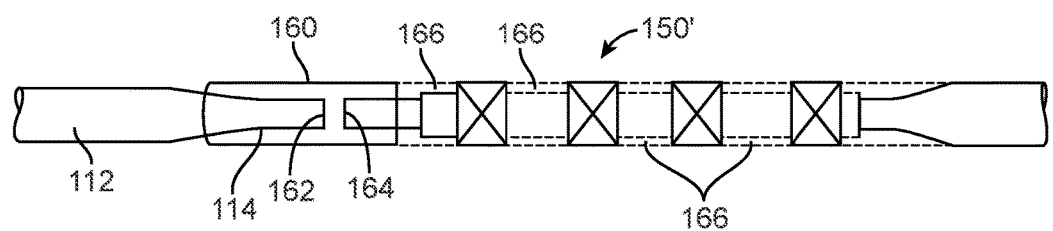
Figure 14C:
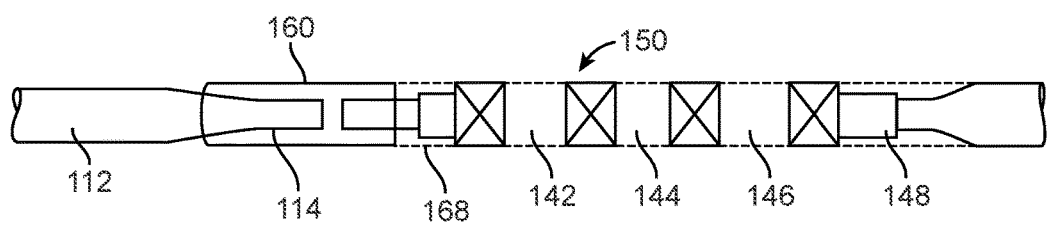

With the subassembly 150' joined to the core wire 112, the portions between the adjacent ring members may be filled with a reflowed or molded polymer 166 to electrically isolate the adjacent electrodes from one another, as shown in the side view of FIG. 14B. In the event that subassembly 150 having the polymeric spacers 142, 144, 146, 148 is used, as shown in the side view of FIG. 14C, the attachment between the core wire 112 and subassembly 150 may be made without having to reflow any polymer. An additional space 168 may also be incorporated for the attachment between the subassembly 150 and collar 160. Using either subassembly 150 or 150', the subassembly (and core wire 112) may be sized (e.g., grinding, laser ablation, etc.) to ensure that the transition between the two assemblies is flush and seamless.

Figure 15A:
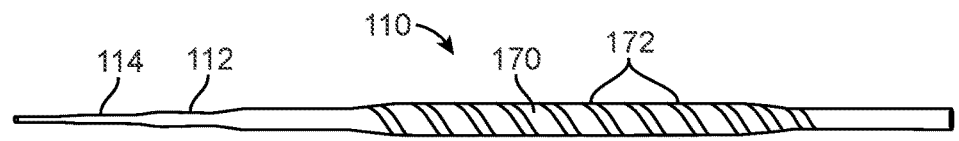
FIGS. 15A to 15C show a core wire have a grooved shaft portion and having the electrode assemblies and covering disposed over the assembly.
Figure 15B:
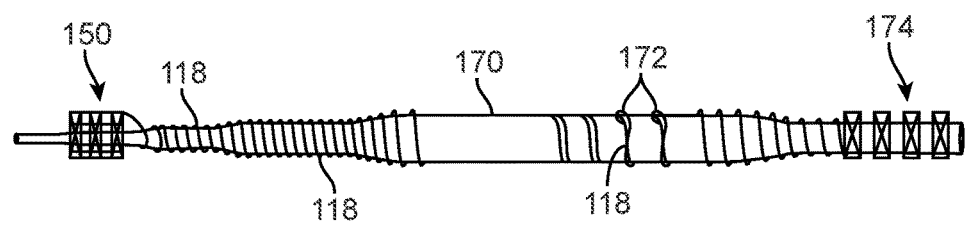

Once the electrodes have been formed or attached to the core wire 110 using any of the methods described herein, the conductive traces or wires 118 extending from the electrode assembly may be attached to the remainder of the core wire 110 using a core wire 110 having a grooved shaft portion 170 proximal to the distal section 114, as shown in the side view of FIG. 15A. The grooved shaft portion 170 may extend over a partial length or a majority of the length of the core wire 110 and define a single helically configured groove 172 having a first pitch. FIG. 15B shows a side assembly view with electrode assembly 150 attached to the distal section 114 of the core wire 110 and a proximal electrode assembly 174 attached to a proximal section of the core wire 110. The conductive traces or wires 118 may be seen wrapped in a helical pattern over the core wire 110. As the conductive traces or wires 118 extend over the grooved shaft portion 170, which may have a relatively larger diameter than the remainder of the core wire, the traces or wires 118 may lie within the groove 172 over the length of the core wire 110, as shown in FIG. 15B.

Figure 15C:
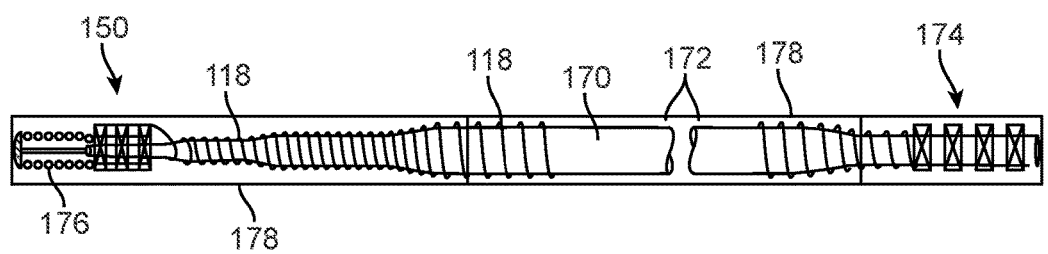

The traces or wires 118 may be wound directly over the portions of the core wire which have a relatively smaller diameter than the grooved shaft portion 170. With the electrode assemblies and traces or wires 118 positioned, the distal coil assembly 176 may be attached to the distal end of the core wire 110 and the distal portion of the core wire 110 having the traces or wires 118 wound directly upon the core wire surface may have a polymer material reflowed upon the assembly to secure it. A covering 178, such as a heat shrink covering made of polyethylene terephthalate (PET), may be disposed over the shaft portion 170 of the core wire over the traces or wires 118 positioned within the grooves 172, as shown in the side view of FIG. 15C. Optionally, the covering 178 may disposed over the entire length of the core wire assembly. With the traces or wires 118 positioned within the groove 172, the resulting guide wire assembly may present a smooth outer surface.

Figure 16A:
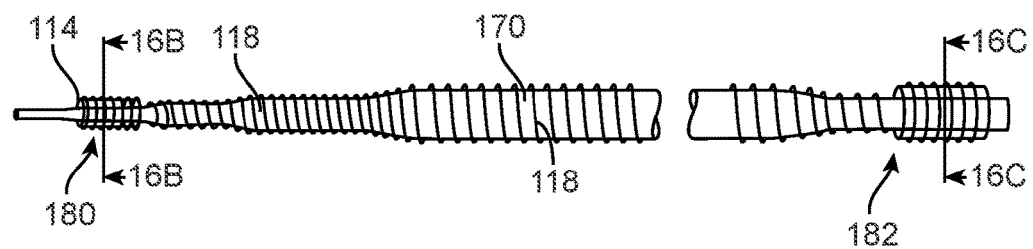
FIGS. 16A to 16C show side and cross-sectional end views of another variation of a core wire having conductive traces or wires positioned upon the core wire at different pitches.
Figure 16B:
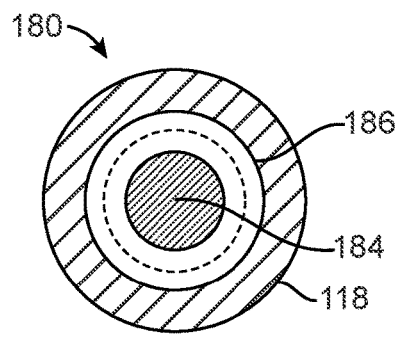
Figure 16C:
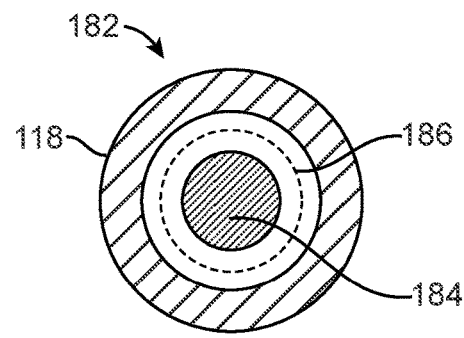

While the traces or wires 118 may be wound upon the core wire at a uniform pitch, they may also be wound upon the core wire at a variable pitch. FIG. 16A shows a side view of one variation where a distal portion of the traces or wires 118 may be wound along the distal portion of the core wire where the electrodes are positioned at a second pitch 180 which is higher and more tightly wound than the first pitch over the remainder of the core wire. The proximal end of the traces or wires 118 where the proximal electrode assembly is positioned upon the core wire may be wound at a third pitch 182 which may be equal to the second pitch 180 at the distal end or different from either the first or second pitch. FIGS. 16B and 16C show cross-sectional end views of the second pitch 180 and third pitch 182 illustrating the core wire 184, an insulative tubing 186 positioned over the core wire 184, and the relatively tightly wound traces or wires 118.

Figure 17A:
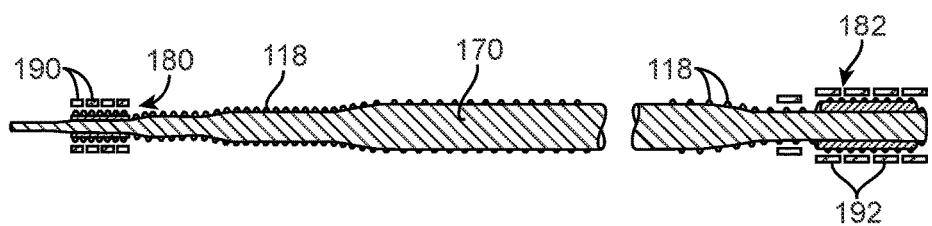
FIGS. 17A and 17B show cross-sectional and side views of a core wire having the electrode assemblies secured to the core wire.
Figure 17B:
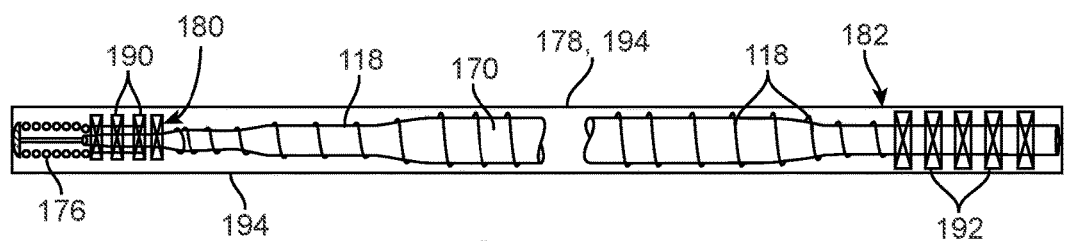

FIG. 17A shows an example of a cross-sectional side view of a core wire having the traces or wires 118 wound helically upon the outer surface of the core wire and examples of distal ring elements 190 secured over the distal portion of the traces or wires 118 as well as proximal ring elements 192 secured over the proximal portion of the traces or wires 118 where the ring elements 190, 192 may be secured upon the assembly utilizing any of the methods described herein. FIG. 17B shows a cross-sectional side view of an example of the resulting overall assembly of the core wire having the wound traces or wires 118, ring elements 190, 192 secured upon the assembly, distal coil 176 attached, and covering 178 disposed over the shaft portion 170, as described above. An additional hydrophilic coating 194 may be disposed over the entire length of the guide assembly assembly.

Figure 18:
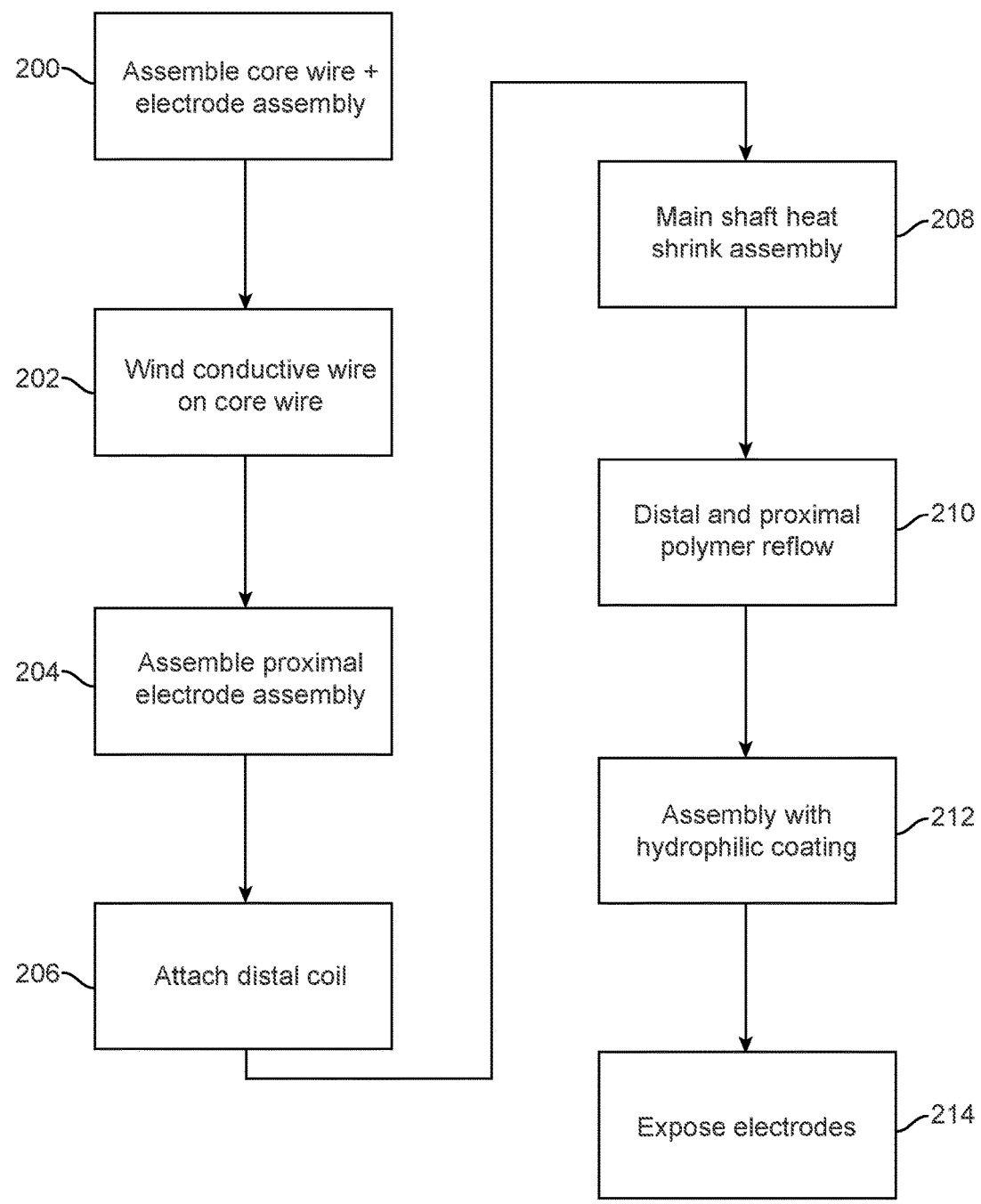
FIG. 18 shows a flow diagram summarizing one variation for assembling a guide wire assembly utilizing any of the methods described herein.

Generally, FIG. 18 shows a flow diagram of a summary of one variation for assembling the resulting guide wire which may be implemented utilizing any of the methods described herein. Once the core wire and electrode assembly for the distal end of the core wire are assembled together 200, the conductive traces or wires may be wound upon the core wire 202 at a uniform pitch or variable pitches. The electrode assembly for the proximal end of the core wire may also be assembled 204. The distal coil may then be attached 206 to the core wire. The main shaft of the core wire may then have a heat shrink covering disposed upon the core wire 208 and the distal and proximal ends of the core wire having the traces or wires positioned over the outer surface of the core wire may have a polymer reflowed upon them 210. An additional hydrophilic coating 212 may be applied over the guidewire assembly and the electrodes and the hydrophilic coating (and/or heat shrink coating if also applied over the distal and/or proximal electrode assemblies) may then be removed from over the electrode assemblies 214 for use.

Figure 19:
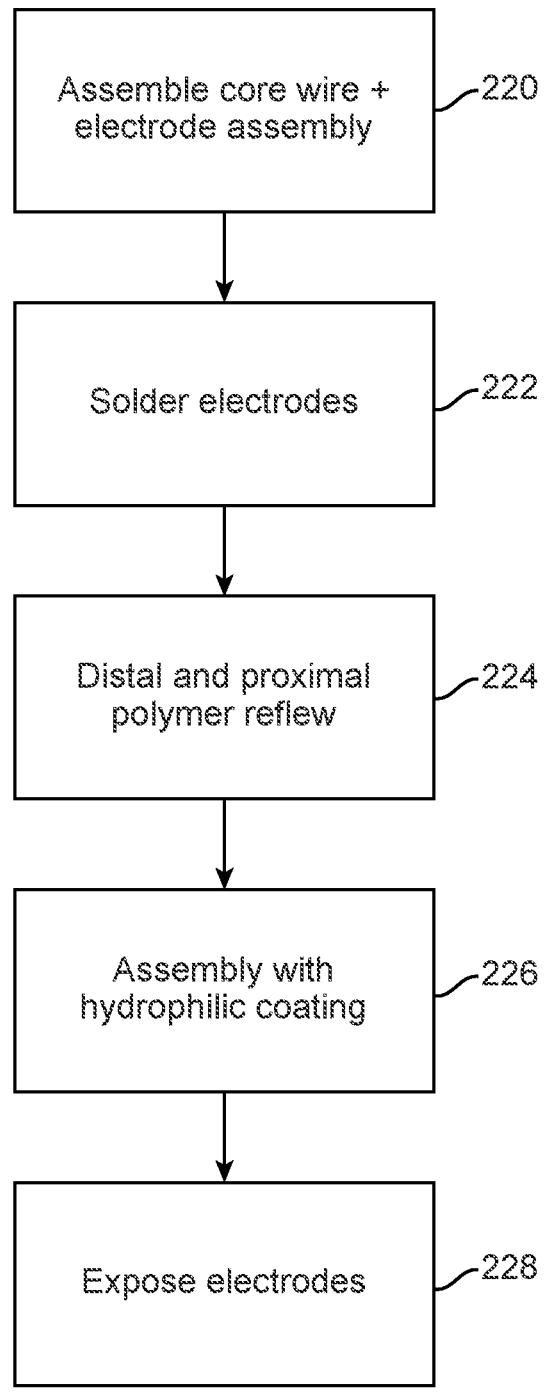
FIG. 19 shows a flow diagram summarizing another variation for assembling a guide wire assembly utilizing any of the methods described herein.

In yet another variation for assembling the resulting guide wire, FIG. 19 shows a flow diagram which may also utilize any of the methods as described herein. Similar to the flow diagram shown in FIG. 18, the core wire and electrode assembly for the distal end (and/or proximal end) of the core wire may be assembled together 220. The ring elements may be attached soldered 222 to form electrodes, as previously described. The portions of the core wire between the ring elements and over the portions of the core wire having the traces or wires may have a polymer reflowed 224 and the assembly may then have a hydrophilic coating applied over the entire guidewire assembly 226. The portions of the hydrophilic coating over the ring elements/electrodes may then be removed to expose the electrodes 228 for use.

The applications of the devices and methods discussed above are not limited to use in guidewires but may include use in any number of other instruments. Modification of the above-described assemblies and methods for carrying out the invention, combinations between different variations as practicable, and variations of aspects of the invention that are obvious to those of skill in the art are intended to be within the scope of the claims.

What is claimed is:

1. A conductive wire assembly, comprising:
   an insulative substrate having a length;
   one or more conductive elements formed along a first direction upon the substrate;
   an insulative coverlay formed upon the one or more conductive elements;
   at least one opening or window defined through the insulative coverlay exposing a portion of the one or more conductive elements; and,
   a conductive coating formed upon the insulative coverlay, wherein the conductive coating is in contact with the portion of the one or more conductive elements through the at least one opening or window,
   wherein the conductive coating has at least one region removed along a second direction in proximity to the at least one opening or window such that one or more conductive pads are formed and are electrically isolated from a remainder of the conductive coating.

2. The assembly of claim 1 wherein the one or more conductive elements are comprised of conductive traces formed upon the insulative substrate.

3. The assembly of claim 1 wherein the insulative coverlay is formed upon the one or more conductive elements and the insulative substrate.

4. The assembly of claim 1 wherein the at least one opening or window is formed corresponding to each conductive element, wherein each opening or window is staggered relative to one another along the first direction.

5. The assembly of claim 1 wherein the conductive coating comprises a metallic coating upon the insulative coverlay.

6. The assembly of claim 1 wherein the at least one region removed is transverse to the first direction.

7. The assembly of claim 6 further comprising additional conductive elements along the first direction upon a second surface of the insulative substrate.

8. The assembly of claim 7 further comprising an additional insulative coverlay upon the additional conductive elements upon the second surface.

9. The assembly of claim 8 further comprising additional openings or windows through the additional insulative coverlay which expose a portion of the additional conductive elements.

10. The assembly of claim 9 further comprising an additional conductive coating upon the additional insulative coverlay.

11. The assembly of claim 10 further comprising additional regions of the additional conductive coating removed along the second direction.

12. The assembly of claim 1 further comprising a core wire upon which the one or more conductive elements are positioned.

13. The assembly of claim 12 further comprising one or more ring elements over corresponding one or more conductive elements such that the one or more ring elements are in electrical communication with the corresponding one or more conductive elements.

14. A conductive wire assembly, comprising:
   one or more conductive elements formed along a first direction;

an insulating layer formed around each of the one or more conductive elements, wherein the one or more conductive elements are secured adjacent to one another along the first direction;

at least one opening or window defined through the insulating layer exposing a portion of the one or more conductive elements; and, a conductive coating formed upon the insulating layer, wherein the conductive coating is in contact with the portion of the one or more conductive elements through the at least one opening or window, wherein the conductive coating has at least one region removed along a second direction in proximity to the at least one opening or window such that one or more conductive pads are formed and are electrically isolated from a remainder of the conductive coating.

15. The assembly of claim 14 wherein the at least one opening or window is formed corresponding to each conductive element, wherein each opening or window is staggered relative to one another along the first direction.

16. The assembly of claim 14 wherein the conductive coating comprises a metallic coating upon the insulating layer.

17. The assembly of claim 14 wherein the at least one region removed is transverse to the first direction.

18. The assembly of claim 14 further comprising additional openings or windows through the insulating layer which expose an additional portion of the one or more conductive elements.

19. The assembly of claim 14 further comprising a core wire upon which the one or more conductive elements are positioned.

20. The assembly of claim 19 further comprising one or more ring elements over corresponding one or more conductive elements such that the one or more ring elements are in electrical communication with the corresponding one or more conductive elements.

21. A method of forming a conductive flat wire, comprising:

securing one or more conductive elements adjacent to one another along a first direction, each of the one or more conductive elements having an insulating layer;

selectively forming at least one opening or window through the insulating layer to expose a portion of the one or more conductive elements;

forming a conductive coating upon the insulating layer such that the conductive coating is in contact with the portion of the one or more conductive elements through the at least one opening or window; and, removing at least one region of the conductive coating along a second direction in proximity to the at least one opening or window such that one or more conductive pads are formed and are electrically isolated from a remainder of the conductive coating.

22. The method of claim 21 wherein forming one or more conductive elements comprises forming one or more conductive traces upon the insulating layer.

23. The method of claim 21 wherein selectively forming at least one opening or window comprises forming an opening or window corresponding to each conductive element, wherein each opening or window is staggered relative to one another along the first direction.

24. The method of claim 21 wherein forming a conductive coating comprises depositing a metallic coating upon the insulating layer.

25. The method of claim 21 wherein removing at least one region comprises removing the at least one region along a second direction which is transverse to the first direction.

26. The method of claim 21 wherein selectively forming at least one opening or window further comprises forming additional openings or windows through the insulating layer to expose an additional portion of the one or more conductive elements.

27. The method of claim 21 further comprising positioning the one or more conductive elements upon a core wire.

28. The method of claim 27 further comprising securing one or more ring elements over corresponding one or more conductive elements such that the one or more ring elements are in electrical communication with the corresponding one or more conductive elements.

29. A method of forming a conductive wire, comprising:

forming one or more conductive elements along a first direction upon an insulative substrate;

forming an insulative coverlay upon the one or more conductive elements;

selectively forming at least one opening or window through the insulative coverlay to expose a portion of the one or more conductive elements;

forming a conductive coating upon the insulative coverlay such that the conductive coating is in contact with the portion of the one or more conductive elements through the at least one opening or window; and, removing at least one region of the conductive coating along a second direction in proximity to the at least one opening or window such that one or more conductive pads are formed and are electrically isolated from a remainder of the conductive coating.

30. The method of claim 29 wherein forming one or more conductive elements comprises forming one or more conductive traces upon the insulative substrate.

31. The method of claim 29 wherein forming an insulative coverlay comprises depositing the insulative coverlay upon the one or more conductive elements and the insulative substrate.

32. The method of claim 29 wherein selectively forming at least one opening or window comprises forming an opening or window corresponding to each conductive element, wherein each opening or window is staggered relative to one another along the first direction.

33. The method of claim 29 wherein forming a conductive coating comprises depositing a metallic coating upon the insulative coverlay.

34. The method of claim 29 wherein removing at least one region comprises removing the at least one region along a second direction which is transverse to the first direction.

35. The method of claim 29 wherein forming one or more conductive elements further comprises forming additional conductive elements along the first direction upon a second surface of the insulative substrate.

36. The method of claim 35 wherein forming an insulative coverlay further comprises forming an additional insulative coverlay upon the additional conductive elements upon the second surface.

37. The method of claim 36 wherein selectively forming at least one opening or window further comprises forming additional openings or windows through the additional insulative coverlay to expose a portion of the additional conductive elements.

38. The method of claim 37 wherein forming a conductive coating further comprises forming an additional conductive coating upon the additional insulative coverlay.

39. The method of claim 38 wherein removing at least one region further comprises removing at least one additional region of the additional conductive coating.

40. The method of claim 29 further comprising positioning the one or more conductive elements upon a core wire.

41. The method of claim 40 further comprising securing one or more ring elements over corresponding one or more conductive elements such that the one or more ring elements are in electrical communication with the corresponding one or more conductive elements.

* * * * *